United States Patent [19]
Butler, Jr. et al.

[11] Patent Number: 6,060,074
[45] Date of Patent: May 9, 2000

[54] METHOD OF CONTROLLING FUNGUS

[75] Inventors: George C Butler, Jr.; Irwin S. Morse, both of Miami, Fla.

[73] Assignee: Morse Enterprises Limited, Inc., Miami, Fla.

[21] Appl. No.: 08/209,268

[22] Filed: Mar. 14, 1994

[51] Int. Cl.$^7$ .................................................. A01N 25/02

[52] U.S. Cl. .......................... 424/405; 424/407; 504/101; 504/116; 47/DIG. 10

[58] Field of Search ..................................... 424/405, 407; 504/116, 101, 189, 320; 47/DIG. 10; 71/24, 903, 904, DIG. 1, DIG. 2

[56] References Cited

U.S. PATENT DOCUMENTS

| | | | |
|---|---|---|---|
| 3,712,802 | 1/1973 | Grybek et al. | 71/79 |
| 3,712,803 | 1/1973 | Grybek et al. | 71/79 |
| 3,884,674 | 5/1975 | Grybek et al. | 71/79 |
| 4,251,255 | 2/1981 | Wagner et al. | 71/27 |
| 5,201,930 | 4/1993 | Campbell | 71/23 |
| 5,393,317 | 2/1995 | Robinson | 71/12 |

*Primary Examiner*—Neil S. Levy
*Attorney, Agent, or Firm*—Banner & Witcoff, Ltd

[57] ABSTRACT

A method of controlling plant infestation by fungus or insects by administering to a plant an aqueous solution that includes a chelating agent, humic acid and an alpha-keto acid.

21 Claims, No Drawings

METHOD OF CONTROLLING FUNGUS

FIELD OF THE INVENTION

The present invention relates to a method for controlling fungus and insects. More particularly, it relates to a method for preventing and treating fungus and insects on fruit bearing plants.

BACKGROUND OF THE INVENTION

Within this application several publications are referenced by arabic numerals within parentheses. Full citations for these references may be found at the end of the specification immediately preceding the claims. The disclosures of these publications in their entireties are hereby expressly incorporated by reference into this application.

Various types of fungus are beneficial to the development of plants. Cooke (1) and Hayman (2). However, agricultural production is significantly reduced worldwide by a large number of pathogenic fungi. Rovira (3) and Moore-Landecker (4). Methods which attenuate these production loses can increase the profits of agricultural businesses and simultaneously provide consumers with a higher quality product at lower cost.

In the past, considerable effort has been devoted to the controlling of pathogenic fungus and destructive insects on plants. Presently, agricultural businesses depend in large measure on the use of fungicides to control fungus. Bonner (5). However, the prior art fungicides are expensive and create health risks for the applicators and for the consumers. Problems have also existed with regard to the control of insects on plants.

The agricultural use of alpha-keto acids is disclosed in U.S. Pat. No. 3,712,802 to Grybek et al., U.S. Pat. No. 3,712,803 to Grybek et al. and U.S. Pat. No. 3,884,674 to Grybek et al., the entire disclosures of which are hereby expressly incorporated by reference. The agricultural use of chelates is disclosed in Chaberek (6).

SUMMARY OF THE INVENTION

A principle object of the invention is to provide a method for controlling fungus and/or insects that includes administering to a plant an aqueous solution including a chelating agent, humic acid and an alpha-keto acid.

Other objects, advantages and features of the present invention will be more readily appreciated and understood when considered in conjunction with the following detailed description and drawings.

DESCRIPTION OF THE PREFERRED EMBODIMENTS

All the disclosed embodiments can be made using conventional compounds and procedures without undue experimentation. All the disclosed embodiments are useful. The invention and various advantageous details thereof are explained more fully below with reference to exemplary embodiments.

The present invention can be used to control a wide variety of fungal infestations. For example, agricultural losses from greasy spot can be caused by Mycosphaererella citri Whiteside. Infestations of Mycosphaerella citri Whiteside can be controlled by the use of the present invention. Similarly, agricultural losses due to post-blossum fruit drop (PFD) in citrus can be caused by the fungus Colletotrichum Gloesporoides. Infestations of Colletotrichum Gloesporoides can be controlled by the use of the present invention.

The present invention can also be used to control a wide variety of insects. For example, damage to new citrus leaves during a leaf flush can be caused by Phyllocnistic citrella Stainton, family Gracillariidae, subfamily Phyllocnistinae (citrus leafminer). Phyllocnistic citrella Stainton can be controlled by the use of the present invention.

The present invention includes a method for controlling fungus or insects by administering to a plant an aqueous solution of a composition including a chelating agent, humic acid and an alpha-keto acid. Two such readily available compositions are KeyPlex and ByPass which are agricultural compositions that contain alpha keto acids, humic acid and glucoheptanate as a chelating agent. The difference between these two compositions is that KeyPlex contains micronutrients. The amount of alpha keto acids is actually greater in ByPass. The amount of glucoheptanate and humic acid are approximately the same.

The alpha-keto acids are of the general formula $R(CH2)[x]COCOOH$, where
x is 0 to 3, preferably 1 or 2, and
R is selected from the group consisting of alkyl, branched or straight chain, aryl, and hetero-N-cyclic.

Among the alpha-keto acids employed in conjunction with the present invention, those which are preferred include phenylpyruvic acid, alpha-keto-phenyl acetic acid, alpha-keto-beta-hydroxy-beta-phenyl propionic acid, beta-hydroxypyruvic acid, alpha-keto-beta-hydroxybutyric acid, indolepyruvic acid, p-hydroxyphenyl pyruvic acid, alpha-keto isovaleric acid, phenyl glyoxylic acid and mixtures thereof.

Humic acid is a brown, polymeric constituent of soils, lignite and peat. Humic acid contains the brownish-black pigment melanin. Humic acid is soluble in bases, but insoluble in mineral acids and alcohols. Humic acid is a mixture of polymers containing aromatic and heterocyclic structures, carboxyl groups, and nitrogen. Humic acid is an excellent chelating agent that is important in the exchange of cations in soils.

Chelating compounds bind to elements and thereby sequester or isolate them from reacting with other elements or combinations of other elements. Sequester and chelate are interchangeable terms. Preferred chelating compounds are glucoheptinates. A particularly preferred chelating compound is citric acid.

The aqueous solution can be administered to plants in a carrier medium. Simultaneous application, even in a single dosage, over an entire field, may be sufficient to result in the control of fungus.

The carrier medium can be simply water or a nutrient or fertilizing liquid in which the alpha-keto acid, the humic acid and the chelating compound are dissolved. The nature of the carrier is of no particular significance to the present invention so long as it does not react with or alter the active components.

The amount of alpha-keto acid required to produce the desired result is quite small. While larger amounts can be used without deleterious effect and, indeed, may even be desirable from the standpoint of materials handling and related parameters, it has not appeared that there is any functional benefit to be obtained from larger dosages. Multiple doses can, however, be useful. Application can be made to foliage, to the root zone, to the soil or by root injection.

While not limited to the following theory, it is theorized that the antifungal and anti-insect results obtained by the use of the aqueous solution containing alpha-keto acids, humic acid and a chelator are due to the aqueous solution enhancing the level of enzymes that are already present in a plant possibly because various plants contain enzymes capable of metabolizing fungal cell walls. Fungal cell walls can include chitin, glucans, and chitosan in varying proportions.

Enzymes of interest include peroxidases, glucanases, chitinases, and chitosanases. These enzymes are often induced in plants by pathogen infection, stress, and certain chemical elicitors.

Spraying the foliage of grapefruit trees with a preferred embodiment of the aqueous solution resulted in a 5% increase in chitinase, a 20.1% decrease in chitosanase, a 14.8% increase in glucanase and a 14.1% increase in peroxidase, in leaf samples compared to a control. After one week, chitinase was 22.6% higher, chitosanase was 2.8% lower, glucanase was 0.6% lower and peroxidase was 12.0% higher, in leaf samples compared to the control. After an additional three weeks, chitinase was 12.7% higher, chitosanase was 112.7% higher, glucanase was 8.4% lower and peroxidase was 11.9% higher, in leaf samples compared to the control.

Injecting grapefruit trees with a preferred embodiment of the aqueous solution resulted in a 23.2% increase in chitinase, a 121.4% increase in chitosanase, a 1.1% increase in glucanase and a 42.5% increase in peroxidase, in the area of injection compared to a control. Similarly, injecting grapefruit trees with another preferred embodiment of the aqueous solution resulted in a 32.2% increase in chitinase, a 171.4% increase in chitosanase, a 6.3% increase in glucanase and a 78.1% increase in peroxidase in the area of injection compared to a control.

Thus, use of the aqueous solution effects the level of the assayed enzymes. Further, the effect is dynamic and long lasting.

EXAMPLES

Specific embodiments of the invention will now be further described by the following, non-limiting examples which will serve to illustrate various features of significance. The examples are intended merely to facilitate an understanding of ways in which the invention may be practiced and to further enable those of skill in the art to practice the invention. Accordingly, the examples should not be construed as limiting the scope of the invention.

EXAMPLE 1

Fungicides were evaluated in a grove of 3-year-old Ruby Red grapefruit (*Citrus paradisi*) on Swingle citrumelo (*Poncirus trifoliata×C. sinensis*) root stock near Lake Alfred, Fla. Each treatment was applied to ten single-tree replications arranged in a randomized complete block design. Ten shoots per tree from the spring flush of growth were tagged in April and 10 shoots from the summer flush were tagged in August. Applications were made on 11 July and repeated on 29 August using a handgun at 250 psi of pressure using about one gallon per tree. The rates and amounts actually applied are given in Table 1.

TABLE 1

Fungicide formulations and adjuvants used with the actual rates per 100 gallons of spray, estimated rates per acre applied on these 3-yr-old trees and equivalent rates per acre for a mature orchard.

| Product | Rate/100 gal | Rate/acre | Equivalent rate/acre (mature orchard) |
|---|---|---|---|
| 1. Aliette 80 WP | 1.0 lb | 1.5 lb | 5.0 lb |
| 2. Rovral 4SC | 0.6 pt | 0.9 pt | 0.38 gal |
| + Triton AG98 | 8.0 oz | — | — |
| 3. Rovral 4SC | 0.8 pt | 1.2 pt | 0.5 gal |
| + Triton AG98 | 8.0 oz | — | — |
| 4. Rovral 4SC | 0.3 pt | 0.45 pt | 0.19 gal |
| + Aliette 80WP | 1.0 lb | 1.5 lb | 5.0 lb |
| 5. Benlate 50DF | 0.4 lb | 0.6 lb | 2.0 lb |
| 6. Citrus Spray Oil (435) | 2.0 gal | 3.0 gal | 10.0 gal |
| 7. Kocide DF | 1.6 lb | 2.4 lb | 8.0 lb |
| 8. Kocide DF | 1.6 lb | 2.4 lb | 8.0 lb |
| + Citrus Spray Oil | 1.0 gal | 1.5 gal | 5.0 gal |
| 9. KeyPlex 350 | 1.6 qt | 2.4 qt | 2.0 gal |
| + ByPass | 0.8 gal | 1.2 gal | 4.0 gal |

The ByPass of trial 9 was applied to the soil around the base of the trees only on 1 July; the KeyPlex 350 of trial 9 was applied to the foliage on both dates as with all other products.

In late December, the growth flush from the previous spring was examined and the percent defoliation determined on the tagged flushes and the percentage of the area affected by greasy spot on the remaining leaves estimated. In March, the previous summer flush was examined and the percentage of the leaf area affected by greasy spot estimated. There was little or no defoliation on any treatment, so this variable was not evaluated on summer flush. In addition, defoliation of the entire tree and the severity of greasy spot symptoms on the remaining leaves was rated on a scale of from 1 to 10 (i.e., 1=none to 10=severe).

Greasy spot severity on the spring flush of growth in this grove was moderate with up to 30% defoliation in December and moderately severe in ratings made prior to the next year's spring flush in March (Table 2). There were only low levels of greasy spot on the summer flush and almost no defoliation on those shoots.

Kocide, Kocide+oil, oil alone, Benlate and KeyPlex 350+ByPass provided the best control of greasy spot. With these products, there was a significant reduction in greasy spot severity and defoliation with all of the variables measured compared to the unsprayed control (Table 2). There were few significant differences among these treatments. Rovral and Aliette, as well as the combination, significantly reduced greasy spot severity and defoliation in some cases, compared to the unsprayed controls. However, Rovral and Aliette treatments were generally less effective than the standard Kocide plus oil treatment. KeyPlex 350+ByPass, a nutritional material with no known fungicidal properties, appeared to be as effective as standard treatments for control of greasy spot.

TABLE 2

Effect of fungicide application on the severity of greasy spot and defoliation of Ruby Red grapefruit.

| Product | Rate per Acre | Spring Flush Defoliation (%) | Spring Flush Greasy Spot (%) | Summer Flush Greasy Spot (%) | Overall Severity Rating (1–10) Defoliation | Overall Severity Rating (1–10) Greasy Spot |
| --- | --- | --- | --- | --- | --- | --- |
| Untreated control | — | 31.1 a | 6.9 a | 3.8 a | 5.6 a | 4.8 ab |
| Aliette 80WP | 5.0 lb | 25.5 ab | 8.2 a | 1.8 bc | 4.7 ab | 3.5 bc |
| Rovral 4SC | 0.38 gal | 23.3 bc | 6.7 a | 1.7 bcd | 4.2 bc | 3.2 cd |
| Rovral 4SC | 0.5 gal | 21.8 bc | 7.6 a | 3.5 a | 6.0 a | 5.5 a |
| Rovral + Aliette | 0.19 gal + 5.0 lb | 21.8 bc | 4.8 b | 1.7 bcd | 4.1 bc | 3.5 bc |
| Benlate 50DF | 2.0 lb | 16.9 cd | 2.4 c | 0.9 cde | 3.2 cd | 1.4 e |
| Citrus Spray Oil | 10.0 gal | 16.2 cd | 2.3 c | 2.4 b | 2.6 de | 2.1 cde |
| Kocide DF | 8.0 lb | 14.0 d | 1.8 c | 0.6 de | 2.0 de | 1.0 e |
| Kocide + Oil | 8.0 lb + 5.0 gal | 15.8 cd | 1.5 c | 0.4 e | 1.4 e | 1.0 e |
| KeyPlex 350 + ByPass | 2.0 gal 4.0 gal | 13.9 d | 0.7 c | 1.3 bcde | 2.5 de | 1.7 e |

Example 2

Fungicides were evaluated in a grove of 4-year-old Ruby Red grapefruit (*Citrus paradisi*) on Swingle citrumelo (*Poncirus trifoliata×C sinensis*) root stock near Lake Alfred, Fla. Each treatment was applied to ten single-tree replications arranged in a randomized complete block design. Ten shoots per tree from the spring flush of growth were tagged in April. All products except ByPass were applied to foliage on 8 July using a handgun at 250 psi of pressure using about one gallon per tree. ByPass was applied to the soil surface using the same sprayer and wetting the root zone under the tree with one gallon of spray on 12 May and 8 July. The rates and amounts actually applied are given in Table 3.

TABLE 3

Fungicide formulations and adjuvants used with the actual rates per 100 gallons of spray, estimated rates per acre applied on these 3-yr-old trees and equivalent rates per acre for a mature orchard.

| Product | Rate/100 gal | Rate/acre | Equivalent rate/acre (mature orchard) |
| --- | --- | --- | --- |
| ByPass (soil) | 0.8 gal | 1.2 gal | 4.0 gal |
| KeyPlex 350 (foliar) | 0.4 gal | 0.6 gal | 2.0 gal |
| ByPass (soil) + | 0.8 gal | 1.2 gal | 4.0 gal |
| KeyPlex 350 (foliar) | 0.4 gal | 0.6 gal | 2.0 gal |
| Citrus spray oil | 1.0 gal | 1.5 gal | 5.0 gal |
| Kocide DF | 1.6 lb | 2.4 lb | 8.0 lb |
| Kocide DF + | 1.6 lb | 2.4 lb | 8.0 lb |
| Citrus spray oil | 1.0 gal | 1.5 gal | 5.0 gal |
| RH-7592 2F + | 0.4 oz | 0.6 oz | 2.0 oz |
| Triton B-1956 | 8.0 oz | — | — |
| RH-7592 2F + | 0.8 oz | 1.2 oz | 4.0 oz |
| Triton B-1956 | 8.0 oz | — | — |
| RH-7592 2F + | 1.6 oz | 2.4 oz | 8.0 oz |
| Triton B-1956 | 8.0 oz | — | — |
| RH-7592 + | 0.8 oz | 2.4 oz | 4.0 oz |
| Citrus spray oil | 1.0 gal | 1.5 gal | 5.0 gal |

In mid-January, the growth flush from the previous spring was examined and the percent defoliation determined on the tagged flushes and the percentage of the area affected by greasy spot on the remaining leaves estimated. In March, all trees were evaluated for the percentage of the leaf area affected on all foliage canopy density on a scale of from 1 to 10 (i.e., 1=only new flush present to 10=full canopy). The amount of leaf litter on the ground was also evaluated on a scale of from 1 to 10 (i.e., 1=none to 10=abundant).

Referring to Table 4, on tagged spring flush leaves, all treatments except ByPass reduced the leaf surface affected by greasy spot. Citrus spray oil at 5 gal/acre was not highly effective, but there were a few significant differences among the other treatments. Defoliation on tagged spring flush was greatest on the untreated control and trees treated with ByPass alone or with citrus spray oil. All other treatments significantly reduced defoliation and there were no significant differences among them.

In the overall tree ratings, only ByPass, citrus spray oil alone, and the low rate of RH-7592 failed to reduce the percentage of the leaf area affected by greasy spot. There were no significant differences among the effective treatments. canopy densities were highest on trees treated with the 4-ox and 8-ox rates of RH-7592, Kocide, Kocide+oil. Only ByPass or KeyPlex applied alone failed to improve canopy density compared to the untreated control. All the RH-7592 treatments, Kocide and Kocide+oil significantly reduced the amount of leaf litter compared to the untreated control.

RH-7592 appeared to be highly effective for greasy spot control and all rates tested compared well with the standard Kocide+oil treatment. This fungicide provided some control even at rates as low as 2 oz/acre and control appeared to improve with increased rate. RH-7592 at 4 oz plus citrus spray oil at 5 gal/acre provided excellent control of greasy spot. ByPass applied to the soil failed to control greasy spot. However, when ByPass is applied to the soil, it is recommended that it be applied via an irrigation system to ensure that, as a solute, it will percolate into the soil and reach the root zone of the tree where it will be assimilated by feeder roots. In this example, ByPass was applied to the soil with a spray machine, but the irrigation system was not turned on until several days afterward. Thus, the ByPass applied in this example probably biodegraded rapidly thereby rendering the particular application ineffectual. KeyPlex 350, which is primarily a nutritional material, significantly reduced greasy spot severity and defoliation in many cases. Kocide alone or Kocide+oil provided effected control of greasy spot severity and defoliation.

TABLE 4

Effect of application of product on the severity of greasy spot and defoliation of Ruby Red grapefruit.

| | | Tagged spring flush | | Overall tree ratings | | |
|---|---|---|---|---|---|---|
| Treatment | Rate/acre | Greasy spot (% leaf area affected) | Defoliation (%) | Greasy spot (% leaf area affected) | Canopy density (1–10) | Leaf litter (1–10) |
| Control | — | 9.8 a** | 23.8 ab | 11.0 a | 2.8 e | 9.4 a |
| ByPass | 4.0 gal | 10.5 e | 26.7 a | 9.2 ab | 3.5 de | 4.3 ab |
| KeyPlex 350 | 2.0 gal | 3.0 bcd | 17.8 bcd | 6.7 bcd | 3.9 de | 3.8 ab |
| ByPass + KeyPlex 350 | 4.0 gal 2.0 gal | 3.9 bc | 14.0 cd | 6.7 bcd | 4.6 bcd | 3.6 ab |
| Citrus spray oil | 5.0 gal | 5.1 b | 20.0 abc | 8.1 ab | 4.2 cd | 4.2 ab |
| Kocide DF | 8.0 lb | 2.0 cd | 14.5 cd | 3.0 d | 5.9 ab | 2.8 b |
| Kocide DF + Citrus Spray oil | 8.0 lb 5.0 gal | 2.2 cd | 16.9 bcd | 5.9 bcd | 5.4 abc | 2.8 b |
| RH-7592 2F | 2.0 oz | 3.2 bcd | 13.0 cd | 7.2 abc | 4.7 bcd | 2.8 b |
| RH-7592 2F | 4.0 oz | 2.5 cd | 13.2 cd | 4.0 cd | 5.3 abc | 2.3 b |
| RH-7592 2F | 8.0 oz | 1.4 cd | 12.8 cd | 4.0 cd | 5.4 abc | 2.2 b |
| RH-7592 2F Citrus spray oil | 4.0 oz 5.0 gal | 1.0 d | 11.8 d | 3.6 cd | 6.2 a | 2.3 b |

**Mean separation by the Waller-Duncan k ratio t-test, $p \leq 0.05$.

While there is shown and described herein certain specific combinations embodying this invention for the purpose of clarity of understanding, the same is to be considered as illustrative in character, it being understood that only preferred embodiments have been shown and described. It will be manifest to those skilled in the art that certain changes, various modifications and rearrangements of the parts may be made without departing from the spirit and scope of the underlying inventive concept and that the same is not limited to the particular forms herein shown and described except insofar as indicated in the scope of the appended claims.

The entirety of everything cited above or below is expressly incorporated herein by reference.

References

1. Biology of Symbiotic Fungi, R., Cooke, (1977), John Wiley & Sons.
2. Interactions between Non-pathogenic Soil Microorganisms and Plants, D. S. Hayman, (1978), Elsevier Pub, Co.
3. Interactions between plant roots and soil microorganisms, A. D. Rovira, (1965), Ann. Rev. Microbiology, 19, 241–266.
4. Fundamentals of the Fungi, E. Moore-Landecker, (1972), Prentice-Hill, Inc.
5. Chemical Background for the Biological Sciences, E. H. White, Prentice-Hall. Plant Biochemistry, J. Bonner, J. E. Varner, Academic Press.
6. Organic Sequestering Agents, S. Chaberek & A. E, Martell, John Wiley & Sons.

What is claimed is:

1. A method of controlling plant infestation by fungus comprising administering to a plant an aqueous solution comprising a chelating agent, humic acid and an alpha-keto acid.

2. The method of claim 1 wherein the chelating agent is a glucoheptinate.

3. The method of claim 2 wherein the chelating agent is citric acid.

4. The method of claim 1 wherein the infestation includes greasy spot.

5. The method of claim 1 wherein the fungus includes Mycosphaererella citri Whiteside.

6. The method of claim 1 wherein the infestation includes post-bloom fruit drop.

7. The method of claim 1 wherein the fungus includes Colletotrichum Gloesporoides.

8. The method of claim 1 wherein the plant is a fruit bearing plant.

9. The method of claim 1 wherein the administering comprises applying the aqueous solution as a foliar spray.

10. The method of claim 1 wherein the administering comprises applying the aqueous solution to an area of ground around the plant as a ground spray.

11. The method of claim 10 further comprising applying moisture to the area of ground around the plant so as to cause the aqueous solution to percolate into the ground and migrate toward roots of the plant.

12. The method of claim 1 wherein the alpha-keto acid comprises at least one member selected from the group consisting of beta-hydroxy pyruvic acid, alpha-keto-beta-hydroxy butyric acid, phenyl pyruvic acid, alpha-keto-phenyl acetic acid, alpha-keto-beta-hydroxy-beta-phenyl propionic acid, alpha-keto-beta hydroxybutyric acid, indolepyruvic acid, p-hydroxyphenyl pyruvic acid, alpha-keto isovaleric acid and phenyl glyoxylic acid.

13. A method of controlling plant infestation by insects comprising administering to a plant an aqueous solution comprising a chelating agent, humic acid and an alpha-keto acid.

14. The method of claim 13 wherein the chelating agent is a glucoheptinate.

15. The method of claim 13 wherein the chelating agent is citric acid.

16. The method of claim 13 wherein the insects include Phyllocnistis citrella Stainton.

17. The method of claim 13 wherein the plant is a fruit bearing plant.

18. The method of claim 13 wherein the administering comprises applying the aqueous solution as a foliar spray.

19. The method of claim 13 wherein the administering comprises applying the aqueous solution to an area of ground around the plant as a ground spray.

20. The method of claim 19 further comprising applying moisture to the area of ground around the plant so as to cause the aqueous solution to percolate into the ground and migrate toward roots of the plant.

21. The method of claim 13 wherein the alpha-keto acid comprises at least one member selected from the group consisting of beta-hydroxy pyruvic acid, alpha-keto-beta-hydroxy butyric acid, phenyl pyruvic acid, alpha-keto-phenyl acetic acid, alpha-keto-beta-hydroxy-beta-phenyl propionic acid, alpha-keto-beta hydroxybutyric acid, indolepyruvic acid, p-hydroxyphenyl pyruvic acid, alpha-keto isovaleric acid and phenyl glyoxylic acid.

* * * * *